US007057091B2

(12) United States Patent
Zou et al.

(10) Patent No.: US 7,057,091 B2
(45) Date of Patent: Jun. 6, 2006

(54) BRASSICA PYRUVATE DEHYDROGENASE KINASE GENE

(75) Inventors: Jitao Zou, Saskatoon (CA); David C. Taylor, Saskatoon (CA); Elizabeth-France Marillia, Asquith (CA)

(73) Assignee: National Research Council of Canada, Saskatoon (CA)

( * ) Notice: Subject to any disclaimer, the term of this patent is extended or adjusted under 35 U.S.C. 154(b) by 408 days.

(21) Appl. No.: 10/222,075

(22) Filed: Aug. 16, 2002

(65) Prior Publication Data

US 2004/0033606 A1 Feb. 19, 2004

(51) Int. Cl.
*A01H 5/00* (2006.01)
*A01H 5/10* (2006.01)
*C12N 15/92* (2006.01)
*C12N 15/82* (2006.01)

(52) U.S. Cl. ............... 800/298; 536/23.2; 536/23.6; 800/278; 800/281

(58) Field of Classification Search .......... 800/295, 800/281; 536/23.1; 435/320.1
See application file for complete search history.

(56) References Cited

U.S. PATENT DOCUMENTS 6,265,636 B1 * 7/2001 Randall et al. ............. 800/284
6,500,670 B1 * 12/2002 Zou et al. ................. 435/320.1

FOREIGN PATENT DOCUMENTS

WO  WO 98/35044  8/1998

OTHER PUBLICATIONS

U.S. Appl. No. 10/642,531, filed Aug. 2003, Marillia et al.*
Kirill M. Popov et al., "Primary Structure of Pyruvate Dehydrogenase Kinase Establishes a New Family of Eukaryotic Protein Kinases." The Journal of Biological Chemistry. vol. 268, No. 35, Issue of Dec. 15, pp. 26602-26606. 1993.
Ramavedi Gudi et al., "Diversity of the Pyruvate Dehydrogenase Kinase Gene Family in Humans," The Journal of Biological Chemistry, vol. 270, No. 48, Issue of Dec. 1, pp. 28989-28994, 1995.
E. Ellen Reid et al., "Pyruvate Dehydrogenase Complex from Higher Plant Mitochondria and Proplastids," Plant Physiol. (1977) vol. 59, pp. 842-848.
Christopher P.L. Grof. et al., "Mitochondrial Pyruvate Dehydrogenase," Plant Physiol. (1995) vol. 108, pp. 1623-1629.
Tom Newman et al., Genes Galore: A Summary of Methods for Accessing Results from Large-Scale Partial Sequencing of Anonymous *Arabidopsis* cDNA Clones, Plant Physiol. (1994) vol. 106, pp. 1241-1255.

2002 Life Technologies Product catalog, 3' RACE System for Rapid Amplification of cDNA Ends, 21-25, 1 page.
2002 Life Technologies Product catalog, 5' RACE System for Rapid Amplification of cDNA Ends, Version 2.0, 21-22, 1 page.
2002 Life Technologies Product catalog, M-MLV Reverse Transcriptase, 16-25, 1 page.
Zou, Jitao et al., "Effects of antisense repression of an *Arabiodopsis thaliana* pyruvate dehydrogenase kinase cDNA on plant development," National Research Council of Canada, Plant Biotechnology Institute, 110 Gymnasium Place, Saskatoon, Saskatchewan, Canada, S7N 0W9, Plant Molecular Biology 41:837-849, 1999, © 1999 Kluwer Academic Plublishers, Printed in the Netherlands.
Zou, Jitao et al., Cloning and characterization of an *Arabidopsis thaliana* mitochondrial pyruvate dehydrogenase kinase gene and effects of antisense repression on plant development and seed oil content. ABIC, Saskatoon, SK, Jun. 9-12, 1998.
Zou, J-T et al., Does Mitochondrially-Generated Acetate Contribute to Plastidial Fatty Acid Biosynthesis? Antisense repression of an *Arabidopsis thaliana* mitochondrial pyruvate dehydrogenase kinase (PDHK) gene and its effects on oil content and plant development, poster and abstract B71; 13th International Symposium on Plant Lipids, Sevilla, Spain, Jul. 5-10, 1998.
Thelen, Jay J. et al., "Pyruvate dehydrogenase kinase from *Arabidopsis thaliana*: a protein histidine kinase that phosphorylates serine residues," Biochem. J. (2000) 349, 195-201, (Printed in Great Britain).
Mooney, Brian P. et al., Biochemistry Department, University of Missouri, Columbia Missouri 65211; and Plant Genetics Research Unit, USDA, ARS, Columbia, Missouri, 65211, "Histidine Modifying Agents Abolish Pyruvate Dehydrogenase Kinase Activity," Biochemical and Biophysical Research Communications, 267, 500-503 (2000).
Thelen, Jay J. et al., "Molecular Analysis of Two Pyruvate Dehydrogenase Kinases from Maize," The Journal of Biological Chemistry, vol. 273, No. 41, Issue of Oct. 9, 1998, pp. 26618-26623.

(Continued)

*Primary Examiner*—David H. Kruse
(74) *Attorney, Agent, or Firm*—TraskBritt

(57) ABSTRACT

The isolation, purification, characterization and use of a mitochondrial pyruvate dehydrogenase kinase (PDHK) gene from *Brassica* spp. Methods of regulating fatty acid synthesis, seed oil content, seed size/weight, flowering time, vegetative growth, respiration rate and generation time using the gene and to tissues and plants transformed with the gene. Transgenic plants, plant tissues and plant seeds having a genome containing an introduced *Brassica* DNA, characterized in that the sequence has been introduced in an antisense or sense orientation, and a method of producing such plants and plant seeds.

21 Claims, No Drawings

OTHER PUBLICATIONS

GenBank Accession No.: AF038585, 1998.

GenBank Accession No.:AF038586, 1998.

Marillia et al., Characterization of an *Arabidopsis thaliana* mitochrondrial pyruvate dehydrogenase kinase gene and effects of antisense repression on plant development, Abstract and poster #24, pp. 99, Proceedings of the Cana dian Society of Plant Physiologists Meeting, Plant Biology Canada '99, Saskatoon, SK, Jun. 19-23, 1999.

Marillia et al., Metabolic Engineering of Brassica Seeds Oils: Improvement of Oil Quality and Quantity and Alteration of Carbon Flux, Plant Genetic Engineering: Toward the Third Millenium, Elsevier Science B.V., pp. 182-188, 2000.

* cited by examiner

SEQUENCE LISTING

```
<160> NUMBER OF SEQ ID NOS: 15

<210> SEQ ID NO 1
<211> LENGTH: 1104
<212> TYPE: DNA
<213> ORGANISM: Brassica napus
<220> FEATURE:
<221> NAME/KEY: misc_feature
<223> OTHER INFORMATION: PDHK cDNA from B. napus

<400> SEQUENCE: 1
atggcggtga agaaggctag cgagatgttt tcgaagagct tgatcgagga cgttcacaga      60
tggggatgca tgaagcagac gggcgtgagc ctcaggtaca tgatggagtt cggttccact     120
cccactgaga gaaaccttct gatctcggcg cagtttcttc acaaggagct tccgattcgg     180
atcgcgaggc gtgcgatcga actcgagacg ctgccttatg gcctctctga gaaacctgcc     240
gtcttgaagg taagagattg gtatgtggag tcattcaggg acatgagagc gtttcctgag     300
atcaaggata ctgctgatga gaaagagttc acacagatga tcaaggctgt taaagtaagg     360
cacaacaacg tggttcccat gatggctctg ggtgtgaacc agctgaagaa aggaatgaaa     420
ctctacgaaa agcttgatga gattcatcag tttcttgatc gcttctactt gtctcgtata     480
gggatccgta tgcttatcgg gcagcatgtt gagttgcata atccaaaccc accacttcac     540
```

```
acagtgggtt acatacacac caagatgtct cctatggagg tggcaaggaa tgctagtgaa    600
gatgcaaggt cgatttgttt cagagagtat ggttctgctc cggagataaa catatatggc    660
gatccaagtt tcacttttcc gtatgttccg acccatttgc atcttatggt gtatgagtta    720
gtcaagaact ctctccgtgc tgtccaagag cggtttgttg actctgatag ggttgcacca    780
ccaatccgta tcattgttgc tgatggaatc gaagatgtta caataaaggt ctcagatgaa    840
ggtggaggta taccgagaag cggtctccct aaaatattca cttacctcta cagcactgca    900
agaaacccac ttgaagaaga tgtggacttg gaaccgctg atgttcccct gactatggct     960
ggttatggtt atggtctgcc tattagtcgc ttgtatgctc gctattttgg tggagatttg    1020
cagatcatat ccatggaagg atacgggact gatgcttact gcacttgtc tcgtcttgga    1080 gactcgcagg agcctttgcc atga                                          1104

<210> SEQ ID NO 2
<211> LENGTH: 1104
<212> TYPE: DNA
<213> ORGANISM: Brassica rapa
<220> FEATURE:
<221> NAME/KEY: misc_feature
<223> OTHER INFORMATION: PDHK cDNA from B. rapa

<400> SEQUENCE: 2
atggcggtga agaaggctag cgagatgttt tcgaagagct tgatcgagga cgttcacaga    60
tggggatgca tgaagcagac gggcgtgagc ctcaggtaca tgatggagtt cggttccact    120
cccactgaga gaaaccttct gatctcggcg cagtttcttc acaaggagct tccgattcgg    180
atcgcgaggc gtgcgatcga actcgagacg ctgccttatg gcctctctga gaaacctgcc    240
gtcttgaagg tgagggattg gtatgtggag tcattcaggg catgagagc gtttcctgag    300 atcaaggata ctgctgatga gaaagagttc actcagatga ttaaggctgt taaagtaagg    360
cacaacaacg tggttcccat gatggctctg ggtgtgaacc agctgaagaa aggaatgaaa    420
ctctacgaaa agcttgatga gattcatcag tttcttgatc gcttctactt gtctcgtata    480
gggatccgta tgcttatcgg gcagcatgtt gagttgcata atccaaaccc accacttcac    540
acagtgggtt acatacacac caagatgtct cctatggagg tggcaaggaa tgctagtgaa    600
gatgcaaggt cgatttgttt cagagagtat ggttctgctc cggagataaa catatatggc    660
gatccaagtt ccactyttcc gtatgttccg acccatttgc atcttatggt gtatgagtta    720
gtcaagaact ctctccgtgc tgtccaagag cggtttgttg actctgatag ggttgcacca    780
ccaatccgta tcattgttgc tgatggaatc gaagatgtta caataaaggt ctcagatgaa    840
ggtggaggta taccgagaag cggtctccct aaaatattca cttacctcta cagcactgca    900
agaaacccac ttgaagaaga tgtggacttg gaaccgctg atgttcccct gactatggct     960
ggttatggtt atggtctgcc tattagtcgc ttgtatgctc gctattttgg tggagatttg    1020
cagatcatat ccatggaagg atacgggact gatgcttact gcacttgtc tcgtcttgga    1080 gactcgcagg agcctttgcc atga                                          1104

<210> SEQ ID NO 3
<211> LENGTH: 1104
<212> TYPE: DNA
<213> ORGANISM: Brassica oleracea
<220> FEATURE:
<221> NAME/KEY: misc_feature
<223> OTHER INFORMATION: PDHK cDNA from B. oleracea

<400> SEQUENCE: 3
```

-continued

```
atggcggtga agaaggctag cgagatgttt tcgaagagct tgatcgagga cgttcacaga      60
tggggatgca tgaagcagac gggcgtgagc ctcaggtaca tgatggagtt cggttccact     120
cccactgaga ggaacctcct gatctcggcg cagtttcttc acaaggagct tccgattcgg     180
atcgcgaggc gtgcgatcga actcgagacg ctgccttatg gcctctctga gaaacctgcc    240
gtcttgaagg taagrgattg gtatgtggag tcattcaggr acatgagagc gtttcctgag     300
atcaaggata ctgctgayga aaagagttc acacagatga ttaaggctgt taaagtaagg     360
cacaacaacg tggttcccat gatggctctg ggtgttaacc agctgaagaa aggaatgaaa     420
ctctacgaaa aactcgatga gattcatcag tttcttgatc gcttctactt gtcacgtata     480
gggatccgta tgcttatcgg gcagcatgtt gagttgcata atccaaaccc accacttcac     540
actgtgggtt acatacacac caagatgtct cctatggagg tggcaaggaa tgcyagtgaa     600
gatgcaaggt cgatttgttt casagagtat ggttctgctc cggagataaa cmtatatggc     660
gatccaagtt tcacctttcc gtatgtacca acccatttgc atcttatggt gtatgagcta    720
gtcaagaact ctctacgtgc tgtccaagag cgatttgttg attctgatag ggttgcacca    780
ccaatccgta tcattgttgc tgatggaatc gaagatgtta caataaaggt ctcagatgaa    840
ggtggaggta taccgagaag cggtctgccc aaaatattca cttacctsta cagcactgca     900
agaaacccgc ttgaagaaga tgtggacttg gaacagctg atgtacccgt gacwatggct     960
ggttatggtt atggtctgcc yattagtcgc ttgtatgctc gatactttgg tggagatttg    1020
cagatcatat ccatgaagg atacgggact gatgcttact gcacttgtc tcgtcttgga    1080
gactcgcaag agcctttgcc atga                                           1104
```

<210> SEQ ID NO 4
<211> LENGTH: 1104
<212> TYPE: DNA
<213> ORGANISM: Brassica carinata
<220> FEATURE:
<221> NAME/KEY: misc_feature
<223> OTHER INFORMATION: PDHK cDNA from B. carinata

<400> SEQUENCE: 4

```
atggcggtga agaaggctag cgagatgttt tcgaagagct tgatcgagga cgttcacaga      60
tggggatgca tgaagcagac gggcgtgagc ctcaggtaca tgatggagtt cggttccact     120
cccactgaga ggaacctcct gatctcggcg cagtttcttc acaaggagct tccgattcgg     180
atcgcgaggc gtgcgatcga actcgagacg ctgccttatg gcctctctga gaaacctgcc    240
gtcttgaagg taagagattg gtatgtggag tcattcaggg acatgagagc gtttcctgag     300
atcaaggata ctgctgatga aaagagttc acacagatga ttaaggctgt taaagtaagg     360
cacaacaacg tggttcccat gatggctctg ggtgttaacc agctgaagaa aggaatgaaa     420
ctctacgaaa aactcgatga gattcatcag ttttttgatc gcttctactt gtcacgtata     480
gggatccgta tgcttatcgg gcagcatgtt gagttgcata atccaaaccc accacttcac     540
actgtgggtt acatacacac caagatgtct ccatggagg tggcaaggaa tgctagtgaa     600
gatgcaaggt cgatttgttt ccgagagtat ggttctgctc cggagataaa catatatggc     660
gatccaagtt tcacctttcc gtatgtacca acccatttgc atcttatggt gtatgagcta    720
gtcaagaact ctctacgtgc tgtccaagag cggtttgttg actctgatag ggttgcacca    780
ccaatccgta tcattgttgc tgatggaatc gaagatgtta caataaaggt ctcagatgaa    840
ggtggaggta taccgagaag cggcctgccc aaaatattca cttacctcta cagcactgca     900
```

```
agaaacccgc ttgaagaaga tgtggacttg ggaacagctg atgtacccgt gactatggct      960
ggttatggtt atggtctgcc tattagtcgc ttgtatgctc gatactttgg tggagatttg     1020
cagatcatat ccatggaagg atacgggact gatgcttact tgcacttatc tcgtcttgga     1080
gactcgcagg agcctttgcc atga                                            1104
```

<210> SEQ ID NO 5
<211> LENGTH: 367
<212> TYPE: PRT
<213> ORGANISM: Brassica napus
<220> FEATURE:
<221> NAME/KEY: misc_feature
<223> OTHER INFORMATION: Deduced amino acid sequence from B. napus PDHK cDNA (SEQ ID NO:1)

<400> SEQUENCE: 5

```
Met Ala Val Lys Lys Ala Ser Glu Met Phe Ser Lys Ser Leu Ile Glu
1               5                   10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
        35                  40                  45

Ser Ala Gln Phe Leu His Lys Glu Leu Pro Ile Arg Ile Ala Arg Arg
    50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Asp Met Arg
                85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Val Pro Met Met
        115                 120                 125

Ala Leu Gly Val Asn Gln Leu Lys Lys Gly Met Lys Leu Tyr Glu Lys
    130                 135                 140

Leu Asp Glu Ile His Gln Phe Leu Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Phe
    210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

Arg Val Ala Pro Pro Ile Arg Ile Ile Val Ala Asp Gly Ile Glu Asp
            260                 265                 270

Val Thr Ile Lys Val Ser Asp Glu Gly Gly Gly Ile Pro Arg Ser Gly
        275                 280                 285

Leu Pro Lys Ile Phe Thr Tyr Leu Tyr Ser Thr Ala Arg Asn Pro Leu
    290                 295                 300

Glu Glu Asp Val Asp Leu Gly Thr Ala Asp Val Pro Leu Thr Met Ala
```

305 310 315 320
Gly Tyr Gly Tyr Gly Leu Pro Ile Ser Arg Leu Tyr Ala Arg Tyr Phe
            325                 330                 335

Gly Gly Asp Leu Gln Ile Ile Ser Met Glu Gly Tyr Gly Thr Asp Ala
            340                 345                 350

Tyr Leu His Leu Ser Arg Leu Gly Asp Ser Gln Glu Pro Leu Pro
            355                 360                 365

<210> SEQ ID NO 6
<211> LENGTH: 367
<212> TYPE: PRT
<213> ORGANISM: Brassica rapa
<220> FEATURE:
<221> NAME/KEY: misc_feature
<223> OTHER INFORMATION: Deduced amino acid sequence from B. rapa PDHK
      cDNA (SEQ ID NO:2)

<400> SEQUENCE: 6

Met Ala Val Lys Lys Ala Ser Glu Met Phe Ser Lys Ser Leu Ile Glu
1               5                   10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
        35                  40                  45

Ser Ala Gln Phe Leu His Lys Glu Leu Pro Ile Arg Ile Ala Arg Arg
    50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Asp Met Arg
                85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Val Pro Met Met
        115                 120                 125

Ala Leu Gly Val Asn Gln Leu Lys Lys Gly Met Lys Leu Tyr Glu Lys
    130                 135                 140

Leu Asp Glu Ile His Gln Phe Leu Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Ser
    210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

Arg Val Ala Pro Pro Ile Arg Ile Ile Val Ala Asp Gly Ile Glu Asp
            260                 265                 270

Val Thr Ile Lys Val Ser Asp Glu Gly Gly Gly Ile Pro Arg Ser Gly
        275                 280                 285

Leu Pro Lys Ile Phe Thr Tyr Leu Tyr Ser Thr Ala Arg Asn Pro Leu
    290                 295                 300

```
Glu Glu Asp Val Asp Leu Gly Thr Ala Asp Val Pro Leu Thr Met Ala
305                 310                 315                 320

Gly Tyr Gly Tyr Gly Leu Pro Ile Ser Arg Leu Tyr Ala Arg Tyr Phe
            325                 330                 335

Gly Gly Asp Leu Gln Ile Ile Ser Met Glu Gly Tyr Gly Thr Asp Ala
            340                 345                 350

Tyr Leu His Leu Ser Arg Leu Gly Asp Ser Gln Glu Pro Leu Pro
        355                 360                 365

<210> SEQ ID NO 7
<211> LENGTH: 367
<212> TYPE: PRT
<213> ORGANISM: Brassica oleracea
<220> FEATURE:
<221> NAME/KEY: misc_feature
<222> LOCATION: (94)..(94)
<223> OTHER INFORMATION: X at position 94 stands for Asn or Asp
<220> FEATURE:
<221> NAME/KEY: misc_feature
<223> OTHER INFORMATION: Deduced amino acid sequence from B. oleracea
      PDHK cDNA (SEQ ID NO:3).

<400> SEQUENCE: 7

Met Ala Val Lys Lys Ala Ser Glu Met Phe Ser Lys Ser Leu Ile Glu
1               5                   10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
        35                  40                  45

Ser Ala Gln Phe Leu His Lys Glu Leu Pro Ile Arg Ile Ala Arg Arg
50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Xaa Met Arg
            85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Val Pro Met Met
        115                 120                 125

Ala Leu Gly Val Asn Gln Leu Lys Lys Gly Met Lys Leu Tyr Glu Lys
    130                 135                 140

Leu Asp Glu Ile His Gln Phe Leu Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Phe
    210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

Arg Val Ala Pro Pro Ile Arg Ile Ile Val Ala Asp Gly Ile Glu Asp
            260                 265                 270
```

Val Thr Ile Lys Val Ser Asp Glu Gly Gly Ile Pro Arg Ser Gly
            275                 280                 285

Leu Pro Lys Ile Phe Thr Tyr Leu Tyr Ser Thr Ala Arg Asn Pro Leu
        290                 295                 300

Glu Glu Asp Val Asp Leu Gly Thr Ala Asp Val Pro Val Thr Met Ala
305                 310                 315                 320

Gly Tyr Gly Tyr Gly Leu Pro Ile Ser Arg Leu Tyr Ala Arg Tyr Phe
                325                 330                 335

Gly Gly Asp Leu Gln Ile Ile Ser Met Glu Gly Tyr Gly Thr Asp Ala
                340                 345                 350

Tyr Leu His Leu Ser Arg Leu Gly Asp Ser Gln Glu Pro Leu Pro
            355                 360                 365

<210> SEQ ID NO 8
<211> LENGTH: 367
<212> TYPE: PRT
<213> ORGANISM: Brassica carinata
<220> FEATURE:
<221> NAME/KEY: misc_feature
<223> OTHER INFORMATION: Deduced amino acid sequence from B. carinata
      PDHK cDNA (SEQ ID NO:4).

<400> SEQUENCE: 8

Met Ala Val Lys Lys Ala Ser Glu Met Phe Ser Lys Ser Leu Ile Glu
1               5                   10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
        35                  40                  45

Ser Ala Gln Phe Leu His Lys Glu Leu Pro Ile Arg Ile Ala Arg Arg
    50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Asp Met Arg
                85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Val Pro Met Met
        115                 120                 125

Ala Leu Gly Val Asn Gln Leu Lys Lys Gly Met Lys Leu Tyr Glu Lys
130                 135                 140

Leu Asp Glu Ile His Gln Phe Phe Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Phe
    210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

-continued

```
Arg Val Ala Pro Pro Ile Arg Ile Ile Val Ala Asp Gly Ile Glu Asp
            260                 265                 270

Val Thr Ile Lys Val Ser Asp Glu Gly Gly Ile Pro Arg Ser Gly
            275                 280                 285

Leu Pro Lys Ile Phe Thr Tyr Leu Tyr Ser Thr Ala Arg Asn Pro Leu
        290                 295                 300

Glu Glu Asp Val Asp Leu Gly Thr Ala Asp Val Pro Val Thr Met Ala
305                 310                 315                 320

Gly Tyr Gly Tyr Gly Leu Pro Ile Ser Arg Leu Tyr Ala Arg Tyr Phe
                325                 330                 335

Gly Gly Asp Leu Gln Ile Ile Ser Met Glu Gly Tyr Gly Thr Asp Ala
            340                 345                 350

Tyr Leu His Leu Ser Arg Leu Gly Asp Ser Gln Glu Pro Leu Pro
        355                 360                 365

<210> SEQ ID NO 9
<211> LENGTH: 27
<212> TYPE: DNA
<213> ORGANISM: Artificial Sequence
<220> FEATURE:
<223> OTHER INFORMATION: Degenerate forward primer with a KpnI site.
<220> FEATURE:
<221> NAME/KEY: misc_feature
<222> LOCATION: (15)..(15)
<223> OTHER INFORMATION: N at position 15 stands for any nucleotide
<220> FEATURE:
<221> NAME/KEY: misc_feature
<222> LOCATION: (16)..(16)
<223> OTHER INFORMATION: N at position 16 stands for any nucleotide

<400> SEQUENCE: 9
cggggtacct ggggnnssat gaarcar                                      27

<210> SEQ ID NO 10
<211> LENGTH: 27
<212> TYPE: DNA
<213> ORGANISM: Artificial Sequence
<220> FEATURE:
<223> OTHER INFORMATION: Degenerate reverse primer with a XbaI site.
<220> FEATURE:
<221> NAME/KEY: misc_feature
<222> LOCATION: (13)..(13)
<223> OTHER INFORMATION: N at position 13 stands for any nucleotide

<400> SEQUENCE: 10
tgctctagat yanggyaarg gytcyts                                      27

<210> SEQ ID NO 11
<211> LENGTH: 21
<212> TYPE: DNA
<213> ORGANISM: Artificial Sequence
<220> FEATURE:
<223> OTHER INFORMATION: 5'RACE GSP1 gene specific primer designed from
      the DNA sequence information provided by RACE-generated fragments.

<400> SEQUENCE: 11
ctttcttcag ctggttcaca c                                            21

<210> SEQ ID NO 12
<211> LENGTH: 29
<212> TYPE: DNA
<213> ORGANISM: Artificial Sequence
<220> FEATURE:
<223> OTHER INFORMATION: 5'RACE GSP2 gene specific primer designed from
      the DNA sequence information provided by RACE-generated fragments.
```

```
-continued

<400> SEQUENCE: 12
gactccacat accaatctct taccttcaa                                              29

<210> SEQ ID NO 13
<211> LENGTH: 23
<212> TYPE: DNA
<213> ORGANISM: Artificial Sequence
<220> FEATURE:
<223> OTHER INFORMATION: 5'RACE GSP3 gene specific primer designed from
      the DNA sequence information provided by RACE-generated fragments.

<400> SEQUENCE: 13
cataaggcag cgtctcgagt tcg                                                    23

<210> SEQ ID NO 14
<211> LENGTH: 25
<212> TYPE: DNA
<213> ORGANISM: Artificial Sequence
<220> FEATURE:
<223> OTHER INFORMATION: 3'RACE GSP1 gene specific primer designed from
      the DNA sequence information provided by RACE-generated fragments.

<400> SEQUENCE: 14
agatgtggac ttgggaaccg ctgat                                                  25

<210> SEQ ID NO 15
<211> LENGTH: 28
<212> TYPE: DNA
<213> ORGANISM: Artificial Sequence
<220> FEATURE:
<223> OTHER INFORMATION: 3'RACE GSP2 gene specific primer designed from
      the DNA sequence information provided by RACE-generated fragments.

<400> SEQUENCE: 15
gttatggtct gcctattagt cgcttgta                                               28
```

BRASSICA PYRUVATE DEHYDROGENASE KINASE GENE

TECHNICAL FIELD

This invention relates to plant genes useful for the genetic manipulation of plant characteristics. More specifically, the invention relates to the identification, isolation, and introduction of genes of *Brassica* PDHK sequences.

BACKGROUND

As described in FIG. 1 of PCT International patent application PCT/CA98/00096 to Zou and Taylor, (International Publication WO98\35044 published Aug. 13, 1998, the contents of the entirety of which and the corresponding U.S. patent application Ser. No. 09/355,912, filed Oct. 15, 1999, are incorporated by this reference), acetyl-CoA plays a central role in mitochondrial respiration and plastidial fatty acid biosynthesis. The pyruvate dehydrogenase complex (PDC) oxidatively decarboxylates pyruvate to yield acetyl-CoA.

Plants have both mitochondrial and plastidial isoforms of the PDC (see also U.S. Pat. No. 6,265,636, to Randall et al (Jul. 24, 2001); which is also incorporated in its entirety by this reference). The mitochondrial pyruvate dehydrogenase complex plays a key role in the regulation of acetyl-CoA generation and availability of acetyl moieties for various catabolic and anabolic reactions in plant cells. The mitochondrial PDC is negatively regulated by phosphorylation of the E1α subunit by pyruvate dehydrogenase kinase (PDHK), and positively regulated by dephosphorylation of the PDC by pyruvate dehydrogenase phosphatase (PDCP). Mitochondrially-generated acetyl moieties can find their way into the respiratory tricarboxylic acid (TCA; Krebs) cycle, but also into the plastid compartment where ultimately, acetate units are used by the enzymes of the fatty acid synthesis (FAS) pathway to synthesize fatty acids. These are eventually incorporated into membrane and also storage glycerolipids.

Zou and Taylor also disclose the identification, isolation and characterization of the pyruvate dehydrogenase kinase (PDHK) (gene and cDNA) sequence from the model plant system *Arabidopsis thaliana* and the utilization of this sequence in the genetic manipulation of plants. Also disclosed is a vector containing the full-length PDHK sequence or a significant portion of the PDHK sequence from *Arabidopsis*, in an anti-sense orientation under control of either a constitutive or a seed-specific promoter, for re-introducing into *Arabidopsis* or for introducing into other plants. Zou and Taylor also provided a method to construct a vector containing the full-length PDHK sequence or a significant portion of the PDHK sequence from *Arabidopsis*, in a sense orientation under control of either a constitutive or a seed-specific promoter, for re-introducing into *Arabidopsis* or for introducing into other plants. Also disclosed were methods for modifying *Arabidopsis* and other plants to change their seed oil content, average seed weight or size, respiration rate during development, vegetative growth characteristics, flowering time or patterns of generative growth, and the period required to reach seed maturity.

As disclosed in, for example, Zou and Taylor, respiration, which involves the consumption of $O_2$ and the catabolism of sugar or other substrates to produce $CO_2$, plays a central role in the process of plant growth in providing reducing equivalents, a source of energy and an array of intermediates (carbon skeletons) as the building blocks for many essential biosynthetic processes. The intermediate products of respiration are necessary for growth in meristematic tissues, maintenance of existing phytomass, uptake of nutrients, and intra- and inter-cellular transport of organic and inorganic materials. Respiration is important to both anabolic and catabolic phases of metabolism.

The pyruvate dehydrogenase complex (PDC) is a particularly important site for regulation of plant respiration. Modification of PDC activity through manipulation of PDHK levels can result in a change in the production or availability of mitochondrially-generated acetyl-CoA or a change in the respiration rate. These changes may in turn affect seed oil content, average seed weight or size, respiration rate during development, vegetative growth characteristics, flowering time or patterns of generative growth, and the period required to reach seed maturity.

Many examples exist of successful modifications to plant metabolism that have been achieved by genetic engineering to transfer new genes or to alter the expression of existing genes, in plants. It is now routinely possible to introduce genes into many plant species of agronomic significance to improve crop performance (e.g., seed oil or tuber starch content/composition; meal improvement; herbicide, disease or insect resistance; heavy metal tolerance; etc.) (Somerville, 1993; Kishore and Somerville, 1993; MacKenzie and Jain, 1997).

The *Brassica* genus includes *Arabidopsis thaliana*. The Brassicaceae family is comprised of a large and diverse group of plant species which are economically very important throughout the world. Three diploid *Brassica* species (*B. rapa, B. oleracea* and *B. nigra*) have hybridised in different combinations to give rise to the three amphidiploid species (*B. napus, B. juncea,* and *B. carinata*). Other *Brassica* species include *B. oleifera, B. balearica, B. cretica, B. elongate, B. tourneforii,* and *B. biennis. B. napus* and *B. rapa* have been improved through breeding programs and are now cultivated as canola crops.

It would be an improvement in the art to isolate and sequence the PDHK gene from various useful species of plants of the Brassicaceae.

DISCLOSURE OF INVENTION

The invention involves the isolation, and characterization of PDHK (gene and cDNA) sequences from *Brassica* species and the utilization of these sequences in the genetic manipulation of plants.

The invention also provides a vector containing the full-length PDHK sequence or a significant portion of PDHK sequences from the Brassicaceae, in an anti-sense orientation under control of either a constitutive or a seed-specific promoter, for re-introduction into *Brassica* species or for introduction into other plants.

The invention further provides a method to construct a vector containing the full-length PDHK sequence or a significant portion of the PDHK sequence from *Brassica* species, in a sense orientation under control of either a constitutive or a seed-specific promoter, for re-introducing into *Brassica* or for introduction into other plants.

The invention also provides methods of modifying *Brassica* and other plants to change their seed oil content, average seed weight or size, respiration rate during development, vegetative growth characteristics, flowering time or patterns of generative growth, and the period required to reach seed maturity.

According to one aspect of the present invention, there is provided isolated and purified deoxyribonucleic acid (DNA)

of SEQ ID NO:1, SEQ ID NO:2, SEQ ID NO:3, and/or SEQ ID NO:4. In this aspect, SEQ ID NO:1 is the nucleotide sequence and the corresponding amino acid sequence (SEQ ID NO:5) of the *Brassica napus* PDHK cDNA. SEQ ID NO:2 is the nucleotide sequence and its corresponding amino acid sequence (SEQ ID NO:6) of the *Brassica rapa* PDHK cDNA. SEQ ID NO:3 is the nucleotide sequence and the corresponding amino acid sequence (SEQ ID NO:7) of the *Brassica oleracea* PDHK cDNA. SEQ ID NO:4 is the nucleotide sequence and the corresponding amino acid sequence (SEQ ID NO:8) of the *Brassica carinata* PDHK cDNA.

In yet another aspect of the invention, there is provided a vector containing SEQ ID NO:1, SEQ ID NO:2, SEQ ID NO:3, or SEQ ID NO:4, or a part thereof, for introduction of the gene, in an anti-sense orientation into a plant cell, and a method for preparing a vector containing SEQ ID NO:1, SEQ ID NO:2, SEQ ID NO:3, or SEQ ID NO:4, or a part thereof, for introduction of the gene in a sense orientation, into a plant cell.

The invention also relates to transgenic plants and plant seeds having a genome containing an introduced DNA sequence of SEQ ID NO: 1, SEQ ID NO:2, SEQ ID NO:3, or SEQ ID NO:4 and a method of producing such plants and plant seeds.

The invention also relates to substantially homologous DNA sequences from plants with deduced amino acid sequences of 25% or greater identity, and 50% or greater similarity, isolated and/or characterized by known methods using the sequence information of SEQ ID NO:1, SEQ ID NO:2, SEQ ID NO:3, or SEQ ID NO:4, as will be appreciated by persons skilled in the art, and to parts of reduced length that are still able to function as inhibitors of gene expression by use in an anti-sense or co-suppression (Jorgensen and Napoli 1994) application. It will be appreciated by persons skilled in the art that small changes in the identities of nucleotides in a specific gene sequence may result in reduced or enhanced effectiveness of the genes and that, in some applications (e.g., anti-sense or co-suppression), partial sequences often work as effectively as full length versions. The ways in which the gene sequence can be varied or shortened are well known to persons skilled in the art, as are ways of testing the effectiveness of the altered genes. All such variations of the genes are therefore claimed as part of the present invention.

Stated more generally, the present invention relates to the isolation, purification and characterization of a mitochondrial pyruvate dehydrogenase kinase (PDHK) genes from the Brassicaceae (specifically *Brassica napus, B. rapa, B. oleracea,* and *B. carinata*) and identifies its utility in regulating fatty acid synthesis, seed oil content, seed size/weight, flowering time, vegetative growth, respiration rate and generation time.

The PDHK of the invention is useful in manipulating PDH activity and the respiration rate in plants. For example, as disclosed in Zou and Taylor, transforming plants with a construct containing the partial PDHK gene in an antisense orientation controlled by a constitutive promoter can result in increased mitochondrial PDH activity, and hence an increased production or availability of mitochondrially-generated acetyl-CoA, or an increased respiration rate.

Additionally, over-expressing the full-length PDHK or a partial PDHK gene in either a sense an antisnese orientation, in a tissue-specific manner, may negatively regulate the activity of mitochondrial PDH, resulting in decreased respiratory rates in tissues, such as leaves or tubers, to decrease maintenance respiration and thereby increase the accumulation of biomass.

Some of the manipulations and deliverables which are possible using the PDHK gene or a part thereof, include, but are not limited to, the following: seeds with increased or decreased fatty acid and oil content; plants exhibiting early or delayed flowering times (measured in terms of days after planting or sowing seed); plants with increased or decreased vegetative growth (biomass); plants with root systems better able to withstand low soil temperatures or frost; plants with tissues exhibiting higher or lower rates of respiration; plants exhibiting an enhanced capacity to accumulate storage compounds in other storage organs (e.g., tubers); plants exhibiting an enhanced capacity to accumulate biopolymers which rely on acetyl moieties as precursors, such a polyhydroxyalkanoic acids or polyhydroxybutyric acids (Padgette et al., 1997).

BEST MODE FOR CARRYING OUT THE INVENTION

The best modes for carrying out the invention are apparent from PCT/CA98/00096 (International Publication WO98\35044), incorporated herein, and from the following description of the results of tests and experiments that have been carried out by the inventors. Related technology is disclosed in the incorporated U.S. Pat. No. 6,265,636 to Randall et al.

All plant cells undergo mitochondrial respiration and this ubiquitous process is affected by the activity of the PDC and its regulators PDHK and PDCP. As disclosed in Zou and Taylor, manipulation of PDHK activity through silencing mechanisms (e.g. antisense RNA technology) using plant transformation can affect, e.g., PDH activity, mitochondrial respiration, seed oil content, flowering time, and growth rate.

A number of ways exist by which genes and gene constructs can be introduced into plants, and a combination of plant transformation and tissue culture techniques have been successfully integrated into effective strategies for creating transgenic crop plants. These methods, which can be used in the present invention, have been extensively reviewed elsewhere (Potrykus, 1991; Vasil, 1994; Walden and Wingender, 1995; Songstad et al., 1995), and are well known to persons skilled in the art. For example, one skilled in the art will certainly be aware that these methods include *Agrobacterium*-mediated transformation by vacuum infiltration (Bechtold et al., 1993) or wound inoculation (Katavic et al., 1994), *Agrobacterium* Ti-plasmid-mediated transformation (e.g., hypocotyl (De Block et al., 1989) or cotyledonary petiole (Moloney et al, 1989) wound infection), particle bombardment/biolistic methods (Sanford et al., 1987; Nehra et al., 1994; Becker et al., 1994) or polyethylene glycol-assisted protoplast transformation (Rhodes et al., 1988; Shimamoto et al., 1989) methods.

As will also be apparent to persons skilled in the art, and as extensively reviewed elsewhere (Meyer, 1995; Datla et al., 1997), it is possible to utilize plant promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Particularly preferred plants for modification according to the present invention include borage (*Borago* spp.), Canola, castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae.

Methods of modulating PDHK content and composition in a plant is described in the incorporated U.S. Pat. No. 6,265,636 B1 to Randall et al. (see, e.g., columns 26 through 30 and 37 through 38).

The invention is further described by use of the following illustrative examples.

EXAMPLE I

The PDHK gene was cloned from *Brassica napus* (cv. Quantum) (SEQ ID NO:1) by Reverse Transcription—Polymerase Chain Reaction (RT-PCR) amplification. Total RNA was extracted from young leaves (Wang and Vodkin, 1994) and cDNA produced by reverse transcription (Life Technologies, Inc., 2002, M-MLV Reverse Transcriptase page 16–25). Using this cDNA and several pairs of degenerate primers (SEQ ID NO:9 and SEQ ID NO:10) designed from conserved segments of known PDHK amino-acid sequences from *Arabidopsis* (CAA07447) and corn (AF038585), a fragment of about 1 kb was amplified by the Polymerase Chain Reaction (PCR). The fragment was cloned into the TOPO cloning vector (pCR TOPO 2.1, Invitrogen) and fully sequenced in both orientations (DNA lab, PBI/NRC). DNA sequence analysis revealed that this amplicon shared a high degree of homology with other known mtPDHK genes.

The missing termini of the gene were subsequently amplified using a 3' and 5' Rapid Amplification cDNA Ends (RACE) kit (Life Technologies, Inc., 2002, 3' RACE system and 5' RACE system pages 21–25). The full-length gene was then produced by PCR using Vent DNA polymerase (New England Biolabs) and gene specific primers (SEQ ID NO:11, SEQ ID NO:12, SEQ ID NO:13, SEQ ID NO:14, and SEQ ID NO:15) designed from the DNA sequence information provided by the RACE-generated fragments. These primers encompassed each end of the gene, ie, the start and stop codons. At this stage, restriction sites were also added by PCR for subsequent anti-sense insertion of the PDHK gene into expression vectors such as pSE129A bearing the napin promoter (PBI/NRC) or pBBV-PHAS with the phaseolin promoter (DowAgro Science). Orientation of the inserted gene was verified by restriction digestions and DNA sequencing.

DNA sequence analyses showed that the *B. napus* PDHK gene has an 1104 bp long open reading frame (386 AA). It was analyzed with respect to other PDHK sequences (GenBank) available and amino-acid comparison revealed 93% and 71% identity with *Arabidopsis* and corn sequences respectively. All DNA analyses (sequence alignments, primer design, etc.) were performed using the DNASTAR Lasergene software package.

EXAMPLE II

The same approach employed for cDNA cloning and sequence analysis of PDHK from *Brassica napus* as described in Example I was followed for the cloning and sequence analysis of the *B. rapa* PDHK gene (SEQ ID NO:2).

EXAMPLE III

The same approach employed for cDNA cloning and sequence analysis of PDHK from *Brassica napus* as described in Example I was followed for the cloning and sequence analysis of the *B. oleracea* PDHK gene (SEQ ID NO:3).

EXAMPLE IV

The same approach employed for cDNA cloning and sequence analysis of PDHK from *Brassica napus* as described in Example I was followed for the cloning and sequence analysis of the *B. carinata* PDHK gene (SEQ ID NO:4).

EXAMPLES V–VIII

The same approach employed for cDNA cloning and sequence analysis of PDHK from *Brassica napus* as described in Example I is followed for the cloning and sequence analysis of PDHK gene from *B. nigra, B. juncea, B. oleifera, B. balearica, B. cretica, B. elongata, B. tourneforii,* and *B. biennis*.

EXAMPLE IX

The oil content of a plant (e.g., borage (*Borago* spp.), Canola, castor (*Ricinus communis*), cocoa bean (*Theobroma cacao*), corn (*Zea mays*), cotton (*Gossypium* spp), Crambe spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae)) is modified by first introducing an anti-sense nucleic acid construct into a plant transformation vector (e.g., one including a plant promoter) to produce a suitable plant transformation vector by means known to those of skill in the art (see, e.g., columns 26 to 30 of the incorporated U.S. Pat. No. 6,265,636 to Randall et al.) The anti-sense nucleic acid construct includes recombinant nucleic acid sequence encoding *Brassica* PDHK (e.g., the nucleic acid sequence of SEQ ID NO:1, SEQ ID NO:2, SEQ ID NO:3, or SEQ ID NO:4). The plant's genome is thus transformed (see, e.g., columns 33 through 37 of the incorporated U.S. Pat. No. 6,265,636) with said modified plant transformation vector. The plant seed is grown, and oil is extracted from the resulting plant seed.

Although described with the use of particular illustrative examples and embodiments, the scope of the invention is to be determined by the appended claims.

REFERENCES

Bechtold, N., Ellis, J. and Pelletier, G. (1993) In planta *Agrobacterium*-mediated gene transfer by infiltration of adult *Arabidopsis thaliana* plants. *C.R. Acad. Sci. Ser. III Sci. Vie,* 316: 1194–1199.

Becker, D., Brettschneider, R. and Lörz, H. (1994) Fertile transgenic wheat from microprojectile bombardment of scutellar tissue. *Plant J.* 5: 299–307.

Datla, R., Anderson, J. W. and Selvaraj, G. (1997) Plant promoters for transgene expression. *Biotechnology Annual Review* 3: 269–296.

De Block, M., De Brouwer, D. and Tenning P. (1989) Transformation of *Brassica napus* and *Brassica oleracea* using *Agrobacterium tumefaciens* and the expression of the bar and neo genes in the transgenic plants. *Plant Physiol.* 91: 694–701.

Jorgensen, R. A. and Napoli, C. A. (1994) Genetic engineering of novel plant phenotypes. U.S. Pat. No. 5,283,184.

Katavic, V., Haughn, G. W., Reed, D., Martin, M. and Kunst, L. (1994) In planta transformation of *Arabidopsis thaliana. Mol. Gen. Genet.* 245: 363–370.

Kishore G. M. and Somerville, C. R. (1993) Genetic engineering of commercially useful biosynthetic pathways in transgenic plants. *Current Opinion in Biotechnology.* 4: 152–158.

MacKenzie, S. L. and Jain, R. K. (1997) Improvement of oils crops via biotechnology. *Recent Res. Dev. In Oil Chem.* 1: 149–158.

Meyer, P. (1995) Understanding and controlling transgene expression. *Trends in Biotechnology,* 13: 332–337.

Moloney, M. M., Walker, J. M. and Sharma, K. K. (1989) High efficiency transformation of *Brassica napus* using *Agrobacterium* vectors. *Plant Cell Rep.* 8: 238–242.

Nehra, N. S., Chibbar, R. N., Leung, N., Caswell, K., Mallard, C., Steinhauer, L. Baga, M. and Kartha K. K. (1994) Self-fertile transgenic wheat plants regenerated from isolated scutellar tissues following microprojectile bombardment with two distinct gene constructs. *Plant J.* 5: 285–297.

Padgette, S. R., Gruys, K. J., Mitsky, T. A., Tran, M., Taylor, N. B., Slater, S. C. and Kishore, G. M. (1997) Strategies for production of polyhydroxyalkanoate polymers in plants. *Plant Physiol. Suppl.,* 114: 3 (abstract 10003).

Potrykus, I. (1991) Gene transfer to plants: Assessment of published approaches and results. *Annu. Rev. Plant Physiol. Plant Mol. Biol.* 42: 205–225.

Rhodes, C. A., Pierce, D. A., Mettler, I. J., Mascarenhas, D. and Detmer, J. J. (1988) Genetically transformed maize plants from protoplasts. *Science* 240: 204–207.

Sanford, J. C., Klein, T. M., Wolf, E. D. and Allen, N. (1987) Delivery of substances into cells and tissues using a particle bombardment process. *J Part. Sci. Technol.* 5: 27–37.

Shimamoto, K., Terada, R., Izawa, T. and Fujimoto, H. (1989) Fertile transgenic rice plants regenerated from transformed protoplasts. *Nature* 338: 274–276.

Somerville, C. R. (1993) Future prospects for genetic modification of the composition of edible oils from higher plants. *Am. J. Clin. Nutr.* 58 (2 Suppl.): 270S–275S.

Songstad, D. D., Somers, D. A. and Griesbach, R. J. (1995) Advances in alternative DNA delivery techniques. *Plant Cell, Tissue and Organ Culture* 40: 1–15.

Vasil, I. K. (1994) Molecular improvement of cereals. *Plant Mol. Biol.* 25: 925–937.

Walden, R. and Wingender, R. (1995) Gene-transfer and plant regeneration techniques. *Trends in Biotechnology* 13: 324–331.

Wang, C-S and Vodkin, L. O. (1994) Extraction of RNA from tissues containing high levels of procyanidins that bind RNA. *Plant Molecular Biology Reporter* 12: 132–145

What is claimed is:

1. An isolated, purified or recombinant nucleic acid encoding a *Brassica* pyruvate dehydrogenase kinase (PDHK) protein, wherein said nucleic acid is selected from the group of nucleic acid sequences consisting of SEQ ID NO:1, SEQ ID NO:2, SEQ ID NO:3, and SEQ ID NO:4.

2. The isolated, purified or recombinant nucleic acid of claim 1, comprising the nucleic acid sequence of SEQ ID NO:1.

3. The isolated, purified or recombinant nucleic acid of claim 1, comprising the nucleic acid sequence of SEQ ID NO:2.

4. The isolated, purified or recombinant nucleic acid of claim 1, comprising the nucleic acid sequence of SEQ ID NO:3.

5. The isolated, purified or recombinant nucleic acid of claim 1, comprising the nucleic acid sequence of SEQ ID NO:4.

6. A method of transforming a plant comprising introducing the isolated, purified or recombinant nucleic acid of claim 1 into the plant.

7. A process for producing a genetically transformed plant seed, said process comprising transforming a plant seed by introducing the nucleic acid of claim 1 into the plant seed.

8. A vector for transforming plant cells comprising the isolated, purified or recombinant nucleic acid of claim 1.

9. A genetically transformed plant, transformed with the vector of claim 8, said genetically transformed plant characterized by exhibiting at least one altered metabolic function, said metabolic function selected from the group consisting of an altered respiration rate compared to a genomically-unmodified plant of the same genotype, an altered seed oil content compared to a genomically-unmodified plant of the same genotype, an altered flowering time compared to a genomically-unmodified plant of the same genotype, an enhanced resistance to cold temperatures compared to a genomically-unmodified plant of the same genotype, an enhanced biomass compared to a genomically-unmodified plant of the same genotype, and an enhanced capacity to accumulate biopolymers compared to a genomically-unmodified plant of the same genotype.

10. A genetically transformed plant seed produced by the process of claim 7, said plant seed exhibiting an altered seed oil content compared to a genomically-unmodified plant seed of the same genotype.

11. A process of producing a transgenic plant, said process comprising introducing the isolated, purified or recombinant nucleic acid sequence of claim 1 into a genome of a plant thus producing a transgenic plant.

12. The process of claim 11, wherein said plant is a member of the group consisting of borage, Canola, castor, cocoa bean, corn, cotton, *Crambe* spp., *Cuphea* spp., flax, *Lesquerella* and *Limnanthes* spp., Linola, nasturtium, *Oenothera* spp., olive, palm, peanut, rapeseed, safflower, soybean, sunflower, tobacco, *Vernonia* spp., wheat, barley, rice, oat, sorghum, rye, or other members of the Gramineae.

13. A method of changing the oil or biopolymer content of a plant, plant storage organ or plant seed, said process comprising:
  introducing a sense or anti-sense nucleic acid construct into a plant transformation vector to produce a modified plant transformation vector, wherein said sense or anti-sense nucleic acid construct comprises the isolated, purified or recombinant nucleic acid of claim 1;
  transforming said plant, plant storage organ or plant seed's genome with said modified plant transformation vector; and
  growing said plant, plant storage organ or plant seed and extracting said oil or biopolymer.

14. An isolated, purified or recombinant nucleic acid encoding a *Brassica* pyruvate dehydrogenase kinase (PDHK) protein comprising a sequence selected from the group consisting of SEQ ID NO:5, SEQ ID NO:6, SEQ ID NO:7, and SEQ ID NO:8.

15. The isolated, purified or recombinant nucleic acid of claim 4, wherein the sequence of said *Brassica* pyruvate dehydrogenase kinase (PDHK) protein is SEQ ID NO:6.

16. The isolated, purified or recombinant nucleic acid of claim 4, wherein the sequence of said *Brassica* pyruvate dehydrogenase kinase (PDHK) protein is SEQ ID NO:7.

17. The isolated, purified or recombinant nucleic acid of claim 4, wherein the sequence of said *Brassica* pyruvate dehydrogenase kinase (PDHK) protein is SEQ ID NO:8.

18. The isolated, purified or recombinant nucleic acid of claim 1 wherein a sequence of said *Brassica* pyruvate dehydrogenase kinase (PDHK) protein is SEQ ID NO:5.

19. A combination of DNA fragments comprising SEQ ID NO: 1, SEQ ID NO: 2, SEQ ID NO: 3 and SEQ ID NO: 4.

20. An isolated, purified or recombinant nucleic acid encoding a *Brassica* pyruvate dehydrogenase kinase (PDHK) protein, wherein said nucleic acid is SEQ ID NO:1.

21. An isolated, purified or recombinant nucleic acid encoding the peptide of SEQ ID NO:5.

* * * * *

UNITED STATES PATENT AND TRADEMARK OFFICE
CERTIFICATE OF CORRECTION

PATENT NO.        : 7,057,091 B2                                              Page 1 of 1
APPLICATION NO. : 10/222075
DATED             : June 6, 2006
INVENTOR(S)       : Jitao Zou, David C. Taylor and Elizabeth-France Marillia It is certified that error appears in the above-identified patent and that said Letters Patent is hereby corrected as shown below:

CLAIM 15, COLUMN 25, LINE 20,        change "claim 4," to --claim 14,--
CLAIM 16, COLUMN 26, LINE 2,         change "claim 4," to --claim 14,--
CLAIM 17, COLUMN 26, LINE 5,         change "claim 4," to --claim 14,--

Signed and Sealed this

Twenty-third Day of December, 2008

JON W. DUDAS
*Director of the United States Patent and Trademark Office*